(12) United States Patent
Leupold et al.

(10) Patent No.: US 11,576,988 B2
(45) Date of Patent: Feb. 14, 2023

(54) STERILE PACKAGING UNIT AND METHOD FOR PRODUCING SAME

(71) Applicant: Sartorius Stedim Biotech GmbH, Goettingen (DE)

(72) Inventors: Marco Leupold, Kassel (DE); Wei Gao, Kassel (DE); Stefan Schlack, Goettingen (DE); Christian Grimm, Heilbad-Heiligenstadt (DE)

(73) Assignee: Sartorius Stedim Biotech GmbH, Goettingen (DE)

( * ) Notice: Subject to any disclaimer, the term of this patent is extended or adjusted under 35 U.S.C. 154(b) by 85 days.

(21) Appl. No.: 17/332,969

(22) Filed: May 27, 2021

(65) Prior Publication Data

US 2021/0283283 A1    Sep. 16, 2021

Related U.S. Application Data

(62) Division of application No. 15/763,609, filed as application No. PCT/EP2016/072536 on Sep. 22, 2016, now Pat. No. 11,045,566.

(30) Foreign Application Priority Data

Sep. 30, 2015    (DE) .................... 10 2015 116 617.8

(51) Int. Cl.
*A61L 2/08*    (2006.01)
*A61L 2/28*    (2006.01)
(Continued)

(52) U.S. Cl.
CPC ............... *A61L 2/087* (2013.01); *A61L 2/28* (2013.01); *C12M 23/28* (2013.01); *C12M 37/00* (2013.01);
(Continued)

(58) Field of Classification Search
CPC ...... C12M 23/12; C12M 23/40; C12M 25/14; C12M 29/10; C12M 29/04;
(Continued)

(56) References Cited

U.S. PATENT DOCUMENTS 8,963,684 B2    2/2015  Nyffeler et al.
2007/0157748 A1    7/2007  Baumfalk et al.
(Continued)

FOREIGN PATENT DOCUMENTS

EP    2 390 203    11/2011
EP    2 503 320    9/2012
(Continued)

*Primary Examiner* — Michael L Hobbs
(74) *Attorney, Agent, or Firm* — Gerald E. Hespos; Michael J. Porco

(57) ABSTRACT

A sterile packaging unit includes a disposable bioprocessing component (20) and a packaging (30). The disposable bioprocessing component (20) has a component wall that encloses a processing space and on which is secured a sensor system (40) with at least one sensor head (T, P, I, L, D) and with attached sensor electronics (42) that include a memory unit (44). The packaging (30) hermetically encloses the disposable bioprocessing component (20) and has a flexible packaging wall. The disposable bioprocessing component (20) and the packaging (30). are sterilized by being jointly irradiated with ionizing radiation. The sensor electronics (42) are connected electrically to a contact unit (34) extending through the packaging wall.

4 Claims, 1 Drawing Sheet

(51) Int. Cl.
*C12M 1/12* (2006.01)
*C12M 1/36* (2006.01)
*C12M 1/00* (2006.01)

(52) U.S. Cl.
CPC ........ *A61L 2202/181* (2013.01); *C12M 41/48* (2013.01)

(58) Field of Classification Search
CPC ......... B01L 3/502715; B01L 3/502738; B01L 3/5085; B01L 2300/0829; B01L 2300/0861; B01L 2300/0645; B01L 2300/0851; A61L 2/087; A61L 2/28; A61L 2202/181
See application file for complete search history.

(56) References Cited

U.S. PATENT DOCUMENTS

2008/0012577 A1   1/2008  Potyrailo et al.
2010/0021993 A1* 1/2010  Wang ................... B01L 3/5457
                                                  156/60
2011/0187388 A1   8/2011  Ossart

FOREIGN PATENT DOCUMENTS

| WO | 00/55599 | 9/2000 |
| --- | --- | --- |
| WO | 2007/109702 | 9/2007 |
| WO | 2009/100192 | 8/2009 |
| WO | 2009/120231 | 10/2009 |
| WO | 2010/010313 | 1/2010 |
| WO | 2015/076741 | 5/2015 |

\* cited by examiner

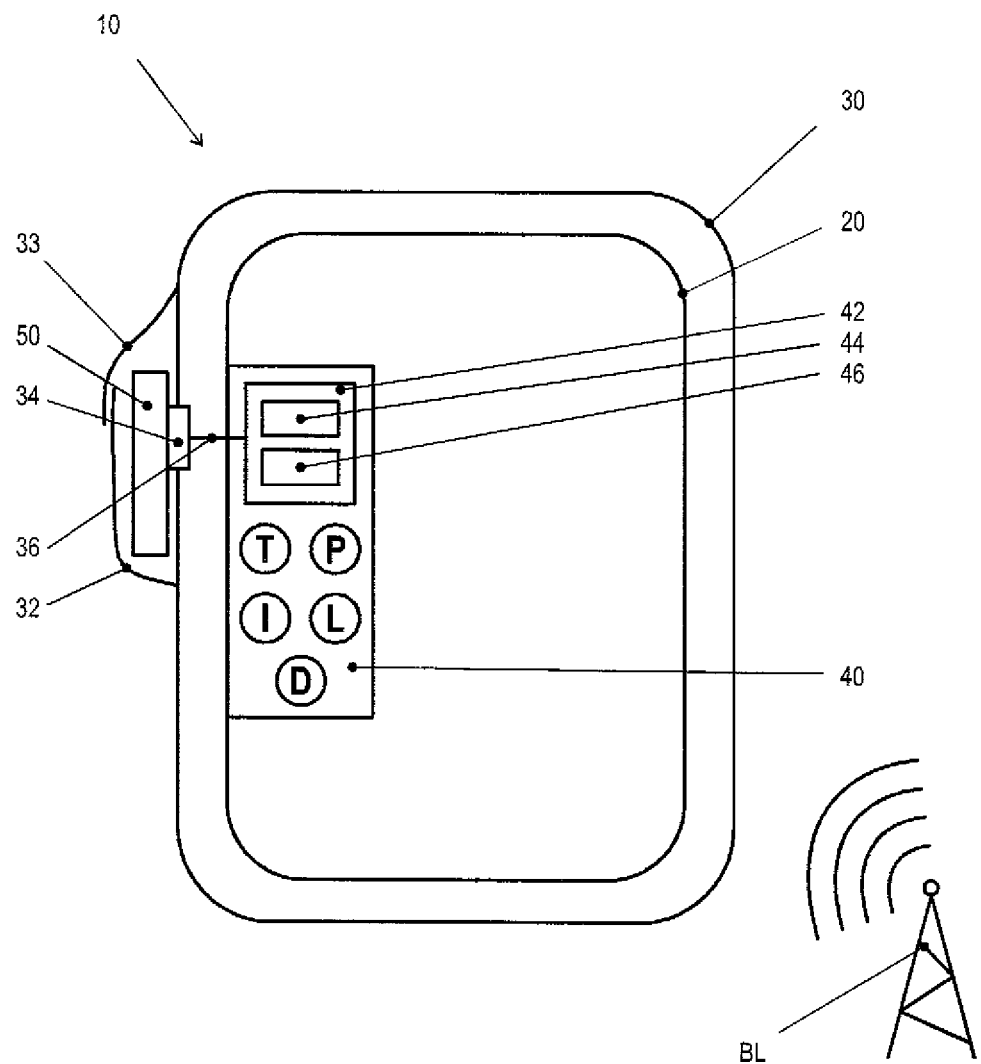

STERILE PACKAGING UNIT AND METHOD FOR PRODUCING SAME

CROSS-REFERENCE TO RELATED APPLICATIONS

This application is a divisional of U.S. patent application Ser. No. 15/763,609, filed on Mar. 27, 2018.

BACKGROUND

Field of the Invention

The present invention relates to a sterile packaging unit, comprising
- a disposable bioprocessing component with a component wall which encloses a processing space and on which is secured a sensor system with at least one sensor head and with attached sensor electronics comprising a memory unit, and
- a packaging which hermetically encloses the disposable bioprocessing component, which are sterilized by being jointly irradiated with ionizing radiation.

Furthermore, the invention relates to a method for producing such packaging unit, comprising the following steps:
- Providing a disposable bioprocessing component with a component wall which encloses a processing space and on which is secured a sensor system with at least one sensor head and with attached sensor electronics comprising a memory unit,
- Hermetically enclosing the disposable bioprocessing component with a packaging and
- Sterilizing disposable bioprocessing component and packaging by joint irradiation with ionizing radiation.

Related Art

U.S. Pat. No. 8,963,684 B2 provides an example of known disposable bioprocessing components.

In the context of the present description, the term bioprocessing component means any component of a system for carrying out bioprocesses. Bioprocessing components with a component wall enclosing a processing space are any kind of receptacles and passages that are suitable for use in bioprocessing systems. These include, in particular: storage containers, bioreactor containers, hoses, valves, pipelines, etc.

In modern pharmaceutical and biotechnology manufacturing methods, disposable components are increasingly used. They can be economically manufactured and—unlike reusable components—do not require expensive cleaning and sterilization after every use. In particular, flexible plastic bags, which may be used as bioreactors or storage containers for bioreactive fluids, for example, are a principal subject of the present invention, even though rigid-wall containers may also be used in accordance with the invention. However, it goes without saying that the present invention also relates to other bioprocessing components which are configured for disposable use, such as: hoses, valves, pipelines, etc. To simplify the explanations given below, reference is frequently made just to said bags. The person skilled in the art will nevertheless understand that the corresponding statements, unless expressly stated otherwise, are also applicable to other types of disposable bioprocessing components.

The aforementioned publication discloses disposable bioprocessing components of this type, which in each case have a sensor system that is secured to the component wall. A sensor head is thus in contact with the processing space and is electrically connected to sensor electronics, which have, among other things, a memory unit. The memory unit is configured as a ferroelectric random access memory (FRAM) in order to be resistant to gamma radiation, which is typically used for the sterilization of the disposable bioprocessing components. Sensor data can be read into the memory unit. A transponder represents an interface between the memory unit and an external peripheral device so that data can be read into the memory unit from outside via the transponder and can be read out from the memory unit to the outside. The manufacturing method for such a disposable bioprocessing component that is described in said publication provides for sterilizing the component using gamma irradiation and activating the sensor electronics after the sterilization step in order to read calibration data into the memory unit. In this process, one may take into account the state of the sensor system, which may have been changed from its original state by the exposure during the gamma sterilization. Alternatively or additionally, it is possible to read additional data, e.g., identification data, from outside into the memory unit. Thus, the sensor electronics are activated in any event by supplying power via the transponder by means of an electromagnetic high-frequency field.

The person skilled in the art knows that such sterile disposable bioprocessing components, in and of themselves, do not constitute sellable products, because contamination would come in again very quickly during storage and handling of the "bare" disposable bioprocessing component. As the person skilled in the art knows, it is therefore absolutely necessary to prepare packaging units from said disposable bioprocessing component and a packaging that hermetically encloses it. In this arrangement, typically and—also within the context of the present invention—preferably, packaging with a flexible packaging wall, in particular flexible plastic bags, are used. The packaging takes place before the sterilization so that packaging and disposable bioprocessing components are jointly irradiated with ionizing radiation (e.g. beta, gamma or x-ray radiation) during the sterilization step and are thereby sterilized. Although the outer side of the packaging undergoes contamination again during further storage and handling, the disposable bioprocessing component hermetically enclosed by the packaging remains sterile. The generic name "sterile packaging unit" that is used here, which by no means also assumes sterility of the packaging outer side, should also be understood in this sense.

It is disadvantageous in the case of the known packaging units that reading data into the memory unit always requires a close physical proximity of the sensor electronics, in particular of the transponder, to an external read-in/read-out unit, which supplies the power for the sensor system in particular via an applied electromagnetic high-frequency field.

The present invention seeks to solve the problem of improving a generic packaging unit and a method for manufacturing the unit in such a way that the sensor electronics can be continuously active even during the storage times of the packaging unit.

SUMMARY

The invention relates to a sterile packaging unit that includes a disposable bioprocessing component and a packaging. The disposable bioprocessing component has a component wall that encloses a processing space and on which a sensor system is secured with at least one sensor head and with attached sensor electronics that include a memory unit. The packaging hermetically encloses the disposable bioprocessing component and has a flexible packaging wall. The disposable bioprocessing component and the packaging are sterilized by being jointly irradiated with ionizing radiation. The sensor electronics are electrically connected to a contact unit extending through the packaging wall.

The invention also relates to a method for producing a sterile packaging unit. The method includes providing a disposable bioprocessing component with a component wall that encloses a processing space and on which is secured a sensor system with at least one sensor head and with attached sensor electronics that include a memory unit. The method also includes hermetically closing the disposable bioprocessing component with a packaging and then sterilizing the disposable bioprocessing component and the packaging by joint irradiation with ionizing radiation. The method further includes electrically connecting the sensor electronics to a contact unit extending through the packaging wall, and the contact unit is connected to an electrical energy storage after the sterilization step.

The invention provides a possibility of durably connecting the sensor electronics to a power source. The obvious measure of integrating a battery in the sensor electronics themselves is out of the question because of the irradiation with ionizing radiation that is required for the sterilization.

The invention therefore takes a different route and provides an electrical connection between the sensor electronics (on the disposable bioprocessing component) and the packaging, wherein a contact unit of this electrical connection extends through the packaging wall, so that the sensor electronics are electrically accessible from outside of the packaging. The person skilled in the art knows techniques on how to apply an electrical conductor in order to, on the one hand, electrically extend through a packaging wall and, on the other hand, not reduce its hermetic protective effect. For example, electrically conductive contact pads can be welded or glued into the packaging wall of a plastic bag.

The electrical accessibility of the sensor electronics from the outside that is created in this way makes it possible to connect a battery or, in general, an electrical energy storage to the sensor electronics only after sterilization by ionizing radiation. On the one hand, the electrical energy storage is not damaged during the irradiation; on the other hand, there is no reason to fear contamination of the disposable bioprocessing components within the context of attaching the electrical energy storage because the latter does not come into contact with the packaging interior.

The contact unit may terminate in a pocket of the packaging wall that is accessible from the outside. In the region of the pocket, the packaging wall therefore has a double-wall design, an inner wall serving to protect the packaging contents and a contact unit extends through it, while the outer packaging wall serves exclusively for the mounting and protection of the electrical energy storage.

The embodiment of the packaging unit according to the invention opens a number of new possibilities of use. The person skilled in the art will recognize that the use of the one-time writing of calibration and identification data into the memory known from the publication discussed at the outset is easily possible also in the case of the packaging unit according to the invention. However, the continuous activation of the sensor electronics by the continuously connected power source enables other forms of use, in particular with regard to recording a history of the disposable bioprocessing component during its lifetime between production and use.

The sensor system may comprise an electrically readable dosimeter. This dosimeter passively records—i.e. without an electrical power supply being required—the radiation exposure during the sterilization process. The control electronics may further comprise a control unit that is configured to read the dosimeter automatically after contacting of the electrical energy storage and to write a read-out dose value into the memory unit automatically, it is possible to check at a later time whether the radiation dose was sufficient for a sterilization or whether the radiation dose was perhaps too high for sensitive elements of the sensor system. This information may, on the one hand, be used as an element of quality management for comprehensive or random-sample checking of the sterilization efficiency before storage of the packaging units. Alternatively or additionally, it can also be used immediately before the use of the disposable bioprocessing component to check its viability.

Because of the continuous supply of power to the sensor system, a nearly seamless monitoring of the storage history of the packaging unit is possible. The sensor system also may comprise at least one environmental parameter sensor and the sensor electronics comprise a control unit that is configured to periodically read the environmental parameter sensor after contacting of the electrical energy storage and to write read-out parameter values together with the corresponding reading time stamps into the memory unit. Some examples of environmental parameter sensors include temperature, pressure and humidity sensors. While the former comprise environmental parameters that act directly on the bioprocessing component and can affect their service life, a humidity sensor can be used to detect possible leaks in the packaging that in the intact state, because of the packaging's hermetic enclosure effect, really should not permit any humidity fluctuations in the region of the sensor system. In the present context, the concept of the environmental parameter sensor should be understood more broadly and can in particular also include sensor systems that interact via transponder technology, for example, with external beacons and record storage positions, for example.

Additional features and advantages of the invention are evident from the following special description and the drawings.

BRIEF DESCRIPTION OF THE DRAWINGS

The FIGURE is a schematic representation of a packaging unit in accordance with the invention.

DETAILED DESCRIPTION

The FIGURE shows an embodiment of a packaging unit 10 according to the invention in a simplified schematic illustration. This embodiment comprises a disposable bioreactor bag 20 and a packaging enclosure 30 that hermetically encloses the disposable bioreactor bag 20. The disposable bioreactor bag 20 supports on its bag wall a sensor system 40 having five sensor heads T, P, I, L, D and having sensor electronics 42 that comprise, in particular, a memory unit 44 configured as FRAM as well as a control unit 46. The sensor heads T, P, I, L, D are connected to the memory unit 44 via a control unit 46. In the depicted embodiment, sensor T is a temperature sensor for the measurement of a temperature in the interior or exterior of the disposable bioreactor bag 20. Sensor P is a pressure sensor for the measurement of a pressure inside or outside of the disposable bioreactor bag 20. Sensor I is an internal sensor for measuring a parameter in the interior of the bioreactor bag 20, e.g., the pH value of a fluid present in the interior of the bioreactor bag 20 during the use of the latter. The sensor L is a location sensor that is capable of communicating with an external locator beacon BL during operation. Sensor D is a passively operating, electrically readable dosimeter that in the passive state is suitable for detecting radiation, in particular gamma radiation, the amount of which in the active state can then be electrically read.

The outer wall of the packaging enclosure 30 is provided with a pocket 32 in which is arranged an electrical energy storage 50, for example a lithium ion rechargeable battery. In the shown embodiment, the pocket 32 is provided with a sealable cover 33 for the protection of the electrical energy storage 50. The electrical energy storage 50 is in electrical contact with a contact pad 34, which is preferably integrally joined to the wall of the packaging enclosure 30 and extends through it. Inside the packaging enclosure 30, the contact pad 34 contacts a conductor 36, which is connected at its other end to the sensor electronics 42 of Sensor 40 so that the electrical energy storage supplies the sensor system 40 with the power required for its operation.

Provided for the production of the packaging unit 10 according to the invention are, first, the bioreactor bag 20 along with sensor system 40 and packaging enclosure 30. Thereafter, the bioreactor bag 20 is inserted in the packaging enclosure 30, and its sensor system 40 is connected via the conductor 36 to the contact pad 34. Then, the packaging enclosure 30 is hermetically sealed. The unit preconfigured in this way undergoes sterilization by being irradiated with ionizing radiation, the amount of radiation being recorded by the passively operating dosimeter D. Following the irradiation, the electrical energy storage 50 is inserted in the pocket 32 and an electrical connection to contact pad 34 is produced. In this way, the sensor system 40 is supplied with power. The reading of the dosimeter is controlled by the control unit 46, and its recorded dose value is read into the memory unit 44. Next, the control unit 46 periodically activates Sensors T, P and L in order to record the corresponding environmental parameters and also to read them into the memory unit 44 together with the measurement time stamps. In this manner, a continuous storage history of the packaging unit 10 is stored in the memory unit 44.

Of course, the embodiments discussed in the specific description and shown in the figures are merely illustrative exemplary embodiments of the present invention. In light of this disclosure, the person skilled in the art is given a wide range of possible variations. In particular, the person skilled in the art will recognize that the connection according to the invention of the sensor electronics 42 to the exterior of the packaging unit 10 can serve not just to supply power to the sensor system 40; it is also possible to additionally implement a data communication channel via which data can be read from the memory unit 44 or written into it.

LIST OF REFERENCE NUMBERS 10 packaging unit
20 bioreactor bag
30 packaging
32 pocket
33 cover of 32
34 contact pad
36 electrical conductor
40 sensor system
42 sensor electronics
44 memory unit
56 control unit
50 electrical energy storage
D dosimeter
T temperature sensor
P pressure sensor
I internal sensor
L location sensor
BL locator beacon

What is claimed is:

1. A method for producing a sterile packaging unit (10), comprising the following steps:
    providing a disposable bioprocessing component (20) with a component wall which encloses a processing space and on which is secured a sensor system (40) with at least one sensor head (T, P, I, L, D) and with attached sensor electronics (42) comprising a memory unit (44),
    hermetically enclosing the disposable bioprocessing component (20) with a packaging (30) and
    sterilizing the disposable bioprocessing component (20) and packaging (30) by joint irradiation with ionizing radiation,
    and, after the sterilizing step, the method further comprising:
    electrically connecting the sensor electronics (42) to a contact unit (34) that extends through the packaging wall and that is connected to an electrical energy storage (50).

2. The method according to claim 1,
wherein: the contact unit (34) terminates in a pocket (32) of the packaging wall accessible from the outside, and the method further comprising positioning the electrical energy storage (50) in the pocket (32) after the sterilization step.

3. The method according to claim 1,
wherein, after the connecting to the electrical energy storage (50), the method further comprises:
    automatically reading an electrically readable dosimeter (D) comprised by the sensor system (40), and then automatically writing a read-out dose value into the memory unit (44).

4. The method according to claim 1,
wherein, after the connecting to the electrical energy storage (50), the method further comprises:
automatically periodically reading an electrically readable environmental parameter sensor (T, P, L) comprised by the sensor system (40), and then automatically writing into the memory unit (44) correspondingly read-out parameter values together with the corresponding reading time stamps.

* * * * *